(12) United States Patent
Jugl et al.

(10) Patent No.: US 9,456,845 B2
(45) Date of Patent: Oct. 4, 2016

(54) NEEDLE ASSEMBLY SYSTEM

(75) Inventors: Michael Jugl, Frankfurt am Main (DE);
Axel Teucher, Frankfurt am Main (DE)

(73) Assignee: Sanofi-Aventis Deutschland GMBH,
Frankfurt am Main (DE)

( * ) Notice: Subject to any disclaimer, the term of this patent is extended or adjusted under 35 U.S.C. 154(b) by 0 days.

(21) Appl. No.: 14/129,508

(22) PCT Filed: Jun. 26, 2012

(86) PCT No.: PCT/EP2012/062284
§ 371 (c)(1),
(2), (4) Date: Dec. 26, 2013

(87) PCT Pub. No.: WO2013/000878
PCT Pub. Date: Jan. 3, 2013

(65) Prior Publication Data
US 2014/0148766 A1 May 29, 2014

(30) Foreign Application Priority Data

Jun. 30, 2011 (EP) .................................... 11172179

(51) Int. Cl.
*A61B 17/34* (2006.01)
*A61M 5/34* (2006.01)
(52) U.S. Cl.
CPC .......... *A61B 17/3417* (2013.01); *A61M 5/347* (2013.01); *A61M 2205/582* (2013.01)
(58) Field of Classification Search
CPC ............ A61B 17/3417; A61M 5/347; A61M 2205/582; A61M 5/34; A61M 2005/3206; A61M 2039/1033
See application file for complete search history.

(56) References Cited

U.S. PATENT DOCUMENTS

| 4,596,561 | A | * | 6/1986 | Meyer | A61M 5/2429 604/190 |
| 4,629,455 | A | * | 12/1986 | Kanno | A61M 5/344 285/332 |
| 2003/0206787 | A1 | * | 11/2003 | Huang | F16B 5/0275 411/412 |
| 2004/0054336 | A1 | | 3/2004 | Klint et al. | |
| 2008/0154192 | A1 | * | 6/2008 | Schraga | A61M 5/50 604/110 |
| 2009/0012479 | A1 | * | 1/2009 | Moller | A61M 5/3155 604/211 |

FOREIGN PATENT DOCUMENTS

| DE | 10254441 A1 | 6/2004 |
| EP | 2039384 A2 | 3/2009 |
| WO | 9739787 A1 | 10/1997 |
| WO | WO 2009137486 A1 * | 11/2009 |

* cited by examiner

*Primary Examiner* — Laura Bouchelle
*Assistant Examiner* — Justin L Zamory
(74) *Attorney, Agent, or Firm* — Fish & Richardson P.C.

(57) ABSTRACT

Described is a needle assembly comprising a needle and a needle hub adapted to carry the needle. The needle hub includes a proximal portion adapted to engage a medicament delivery device having a first thread and a cover portion adapted to abut a distal surface of the delivery device. The proximal portion includes a second thread adapted to engage the first thread, and the second thread is offset from the cover portion by a first distance.

20 Claims, 2 Drawing Sheets

NEEDLE ASSEMBLY SYSTEM

CROSS REFERENCE TO RELATED APPLICATIONS

The present application is a U.S. National Phase Application pursuant to 35 U.S.C. §371 of International Application No. PCT/EP2012/062284 filed Jun. 26, 2012, which claims priority to European Patent Application No. 11172179.1 filed Jun. 30, 2011. The entire disclosure contents of these applications are herewith incorporated by reference into the present application.

FIELD OF INVENTION

The invention relates to a needle assembly system for a medicament delivery device.

BACKGROUND

Patients suffering from diseases like diabetes have to frequently self-administer injections. Medicament delivery devices like pen injectors, auto-injectors and safety syringes have been developed to facilitate self-administering injections. Typically, such delivery devices contain a predetermined amount of medicament and are discarded after use or contain replaceable cartridges of medicament. The delivery devices are re-usable and refitted with sterile injection needle assemblies to minimize the risk of infections.

A conventional needle assembly is screwed onto the delivery by a threaded connection. However, users are unaware of a proper amount of torque to secure the needle assembly to the delivery device, and as a result, typically over-tighten the needle assembly. Over-tightening can result injury (e.g., needlestick) while attaching or removing the needle assembly to/from the delivery device. Also, over-tightening may structurally impair the delivery device. Thus, there is a need for a needle assembly system which induces the use of the proper amount of torque to engage the needle assembly and the delivery device.

SUMMARY

It is an object of the present invention to provide needle assembly system for a medicament delivery device.

In an exemplary embodiment, a needle assembly comprises a needle and a needle hub adapted to carry the needle. The needle hub includes a proximal portion adapted to engage a medicament delivery device having a first thread, and a cover portion adapted to abut a distal surface of the delivery device. The proximal portion includes a second thread adapted to engage the first thread, and the second thread is offset from the cover portion by a first distance.

In an exemplary embodiment, the first thread extends along a distal portion of the delivery device for a second distance. The first distance may be substantially equivalent to the second distance. The first distance may be less than a full length of the proximal portion.

In an exemplary embodiment, the second thread is adapted to engage a third thread on the delivery device. The third thread may be proximal of the first thread. The third thread may have a same pitch as the first thread.

In an exemplary embodiment, the second thread may be adapted to engage one or more ribs on the delivery device. One or more ribs (2.8) may be proximal of the first thread.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
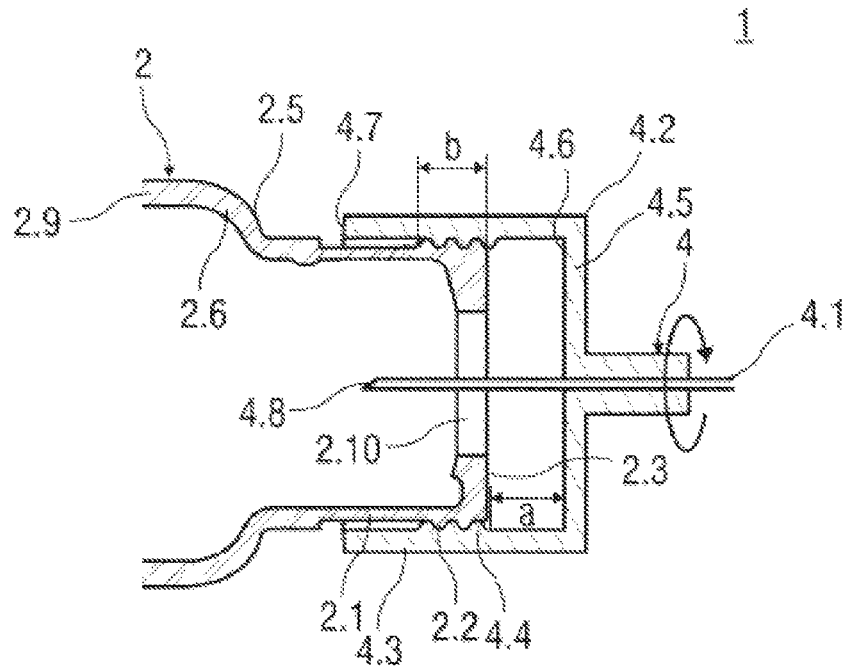
FIG. 1 shows a longitudinal section of parts of a needle assembly system according to an exemplary embodiment of the invention.
Figure 2:
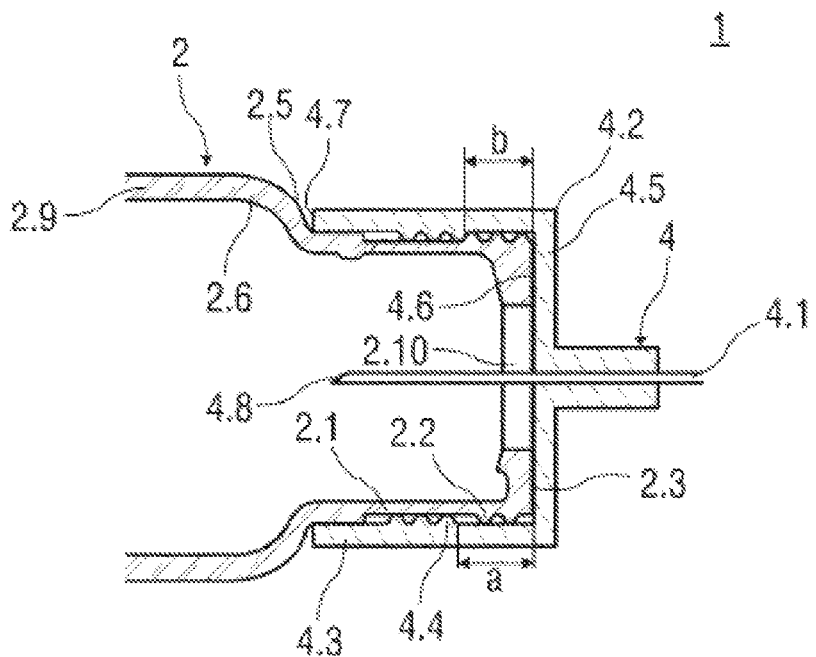
FIG. 2 shows a longitudinal section of parts of a needle assembly system according to an exemplary embodiment of the invention.

FIGS. 1 and 2 show longitudinal sections of an exemplary embodiment of a needle assembly system 1. In an exemplary embodiment, the system 1 includes a medicament delivery device 2 and a needle assembly 4 which is mountable on a distal portion 2.1 thereof. Those of skill in the art will understand that the delivery device 2 may be, but is not limited to, a pen injector, an auto-injector and a safety syringe. Further, although the exemplary embodiment in FIG. 1 shows the needle assembly 4 attaching to the distal portion 2.1 of the delivery device 2, those of skill in the art will understand that the needle assembly 4 may attach to a medicament cartridge and/or an adapter on the cartridge or the distal portion 2.1 of the delivery device 2.

FIG. 1 shows the system 1 while the needle assembly 4 is being mounted on the distal portion 2.1 of the delivery device 2. FIG. 2 shows the system 1 in a mounted state in which the needle assembly 4 is mounted on the delivery device 2, and an injection can be administered.

In an exemplary embodiment, the distal portion 2.1 of the delivery device 2 may have a substantially cylindrical shape and a distal opening 2.10. A shoulder 2.6 of the delivery device 2 connects the distal portion 2.1 and a body portion 2.9. In an exemplary embodiment, the body portion 2.9 has the shape of cylinder which has a larger diameter than the distal portion 2.1. In an exemplary embodiment, the distal portion 2.1 has a first thread 2.2 which extends over a second axial distance b from approximately a midpoint of the distal portion to a distal surface 2.3.

In an exemplary embodiment, the needle assembly 4 includes a needle 4.1 and a needle hub 4.2 which carries the needle 4.1. The needle hub 4.2 may have a cylindrical proximal portion 4.3 which is adapted to engage the distal end 2.1 of the delivery device 2 and a cover portion 4.5 which is adapted to abut the distal surface 2.3 of the delivery device 2. The needle 4.1 may pass through the cover portion 4.5 so that, when the needle assembly 4.1 engages the delivery device 2, a proximal end 4.8 extends into a medicament cartridge. An inner surface of the needle hub 4.2 may have a second thread 4.4 which originates at a first axial distance a from a proximal surface 4.6 of the cover portion 4.5. In an exemplary embodiment, the first distance a is substantially equivalent to the second distance b.

In an exemplary embodiment, an inner diameter of the proximal portion 4.3 of the needle hub 4.2 is substantially equivalent to an outer diameter of the distal portion 2.1 of the delivery device 2 so that the distal portion 2.1 can be inserted into the proximal portion 4.3 of the needle hub 4.2 until the first thread 2.2 abuts the second thread 4.4.

In an exemplary embodiment, to mount the needle assembly 4 on the delivery device 2, the distal portion 2.1 of the delivery device 2 is inserted into the proximal portion 4.3 of the needle hub 4.2 until the first thread 2.2 abuts the second thread 4.4 of the needle hub 4. Then, rotation of the needle hub 4.2 relative to the delivery device 2 causes the first thread 2.2 to engage the second thread 4.4, as shown in the exemplary embodiment depicted in FIG. 1. After several rotations (corresponding to the number of threads), the delivery device 2 is engaged in the needle hub 4.2 such that the distal surface 2.3 of the delivery device 2 abuts on the proximal surface 4.6 of the cover portion 4.5, as shown in the exemplary embodiment depicted in FIG. 2.

As shown in the exemplary embodiment in FIG. 2, the first and second distances a and b are substantially equivalent such that first thread 2.2 and the second threads 4.4 are disengaged from each other in a mounted state of the system 1. Thus, in the mounted state, further rotation of the needle assembly 4 relative to the delivery device 2 does not further tighten the needle assembly 4 on the delivery device 2. In the mounted state, the proximal end 4.8 of the needle 4.1 extends through the distal opening 2.10 into the medicament cartridge in the delivery device 2 so that the medicament can be delivered.

As shown in the exemplary embodiment in FIG. 2, a notch is formed in the distal portion 2.1 of the delivery device 2 proximal of the first threads 2.2. A length of the notch may be substantially equivalent to the length of the second thread 4.4. The notch may, therefore, provide abutment surfaces to prevent the needle assembly 4 from sliding on the distal portion 2.1.

Figure 3:
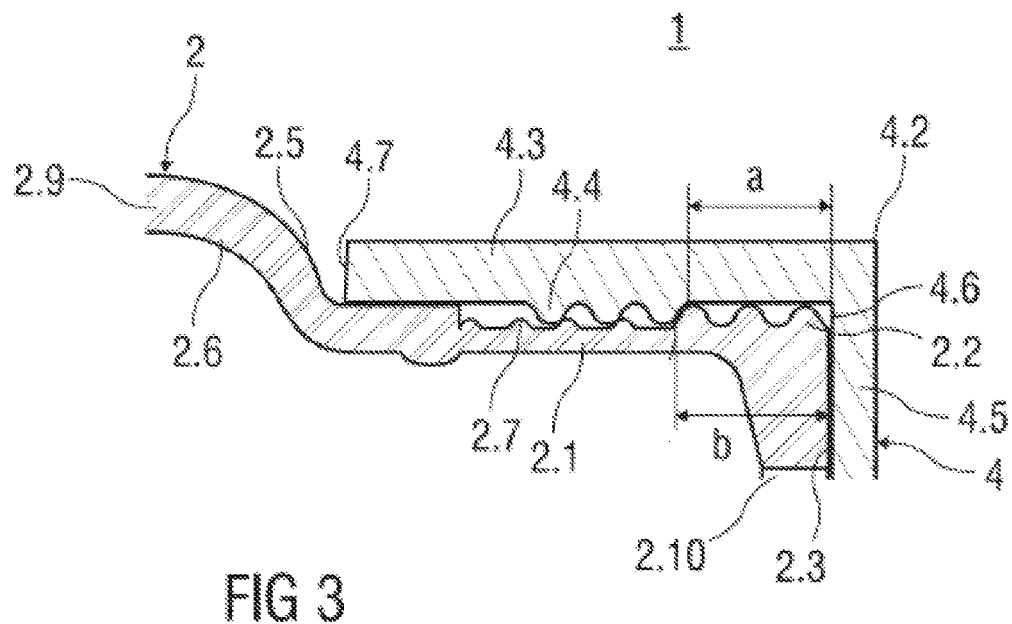
FIG. 3 shows a longitudinal section of parts of a needle assembly system according to another exemplary embodiment of the invention.

FIG. 3 shows a longitudinal section of parts of another exemplary embodiment of a needle assembly system 1 according to the present invention. In this exemplary embodiment, a third thread 2.7 is formed on the distal portion 2.1 proximal of the first thread 2.2. The third thread 2.7 has the same pitch as, but a smaller depth than, the first thread 2.2. The third thread 2.7 may be formed in the notch. In this exemplary embodiment, the second thread 4.4 can slide over the third thread 2.7 while the needle assembly 4 is mounted on the delivery device 2 as described above. Furthermore, as shown in the exemplary embodiment in FIG. 3, the third thread 2.7 is arranged so that in the mounted state, the third thread 2.7 abuts the second thread 4.4 of the needle assembly 4.

When the second thread 4.4 engages the third thread 2.7, a tactile feedback may be provided which indicates that the needle assembly 4 is nearly mounted to the delivery device 2. The third thread 2.7 may also support alignment of the needle assembly 4 and the first and second threads 2.2 and 4.4 during the mounting process. The third thread 2.7 may also produce a biasing force between the needle assembly 4 and the delivery device 2 to compensate tolerances caused by deviations of the first and second distances a or b from their scheduled values.

Figure 4:
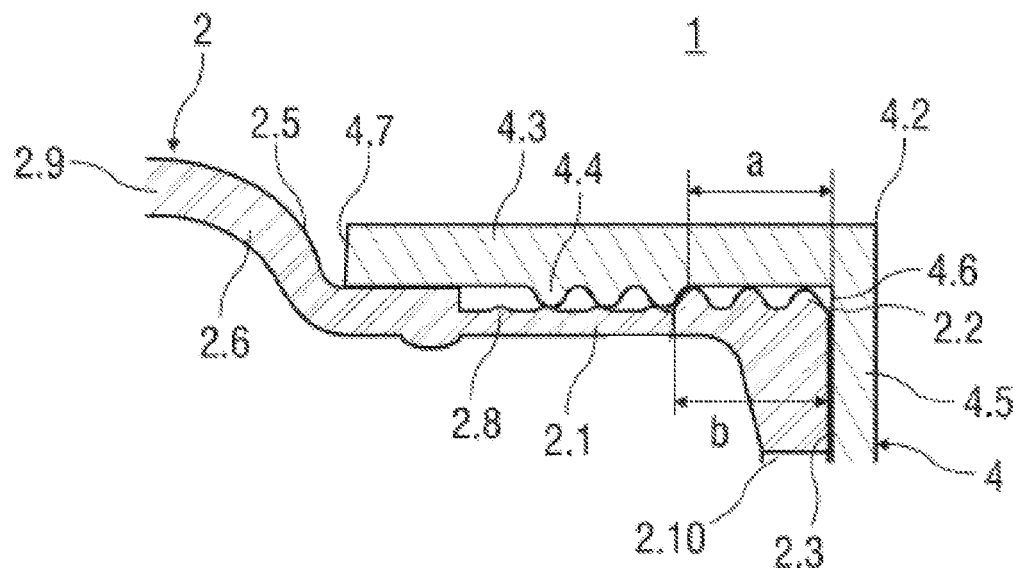
FIG. 4 shows a longitudinal section of parts of a needle assembly system according to another exemplary embodiment of the invention.

FIG. 4 shows a longitudinal section of parts of another exemplary embodiment of a needle assembly system 1 according to the present invention. In this exemplary embodiment, one or more ribs 2.8 are formed on the distal portion 2.1 proximal of the first thread 2.2. A depth of the ribs 2.8 may be smaller than the depth of the first thread 2.2 so that the second thread 4.4 can slide over the ribs 2.8 while the needle assembly 4 is mounted on the delivery device 2. Furthermore, as shown in the exemplary embodiment in FIG. 4, the ribs 2.8 are arranged so that in the mounted state, the ribs 2.8 abut the second thread 4.4 of the needle assembly 4.

When the second thread 4.4 engages the ribs 2.8, a tactile feedback may be provided which indicates that the needle assembly 4 is nearly mounted to the delivery device 2. The ribs 2.8 may also support alignment of the needle assembly 4 and the first and second threads 2.2 and 4.4 during the mounting process. The ribs 2.8 may also produce a biasing force between the needle assembly 4 and the delivery device 2 to compensate tolerances caused by deviations of the first and second distances a or b from their scheduled values.

In an exemplary embodiment, a proximal face 4.7 of the proximal portion 4.3 of the needle assembly 4 may abut the shoulder surface 2.5 of the shoulder 2.6 of the delivery device 2 to provide a stop, limiting axial movement of the needle assembly 4 relative to the delivery device 2.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:
1. A needle assembly system comprising:
a medicament delivery device; and
a needle assembly mountable on a distal portion of the medicament delivery device, the needle assembly comprising:
a needle;
a needle hub adapted to carry the needle, wherein the needle hub includes:
a proximal portion adapted to engage the medicament delivery device; and
a cover portion adapted to abut a distal surface of the medicament delivery device,
wherein the proximal portion of the needle hub includes a second thread adapted to engage a first thread of the medicament delivery device,
wherein the second thread is offset from the cover portion by a first distance, the first thread extends along the distal portion of the medicament delivery device for a second distance, and the first distance is substantially equivalent to the second distance,
wherein the distal portion of the medicament delivery device comprises (i) an unthreaded region extending proximally from the first thread or (ii) a threaded region extending proximally from the first thread and having a third thread with a depth less than a depth of the first thread, and
wherein the first thread is configured to be threadedly disengaged from the needle assembly and the second thread is configured to be positioned over the unthreaded region or the threaded region of the distal portion of the medicament delivery device when the needle assembly is mounted on the medicament delivery device.

2. The needle assembly system according to claim 1, wherein the first distance is less than a full length of the proximal portion.

3. The needle assembly system according to claim 1, wherein the distal portion of the medicament delivery device comprises the threaded region, and the second thread is adapted to engage the third thread on the medicament delivery device.

4. The needle assembly system according to claim 3, wherein the third thread has a same pitch as the first thread.

5. The needle assembly system according to claim 1, wherein the second thread is adapted to engage one or more ribs on the medicament delivery device.

6. The needle assembly system according to claim 5, wherein the one or more ribs is proximal of the first thread.

7. The needle assembly system according to claim 1, wherein a distal end of the second thread is configured to be proximal to a proximal end of the first thread when the needle assembly is mounted on the medicament delivery device.

8. The needle assembly system according to claim 1, wherein the medicament delivery device is an auto-injector.

9. The needle assembly system according to claim 1, wherein, when the needle assembly is mounted on the medicament delivery device, the first thread and the second thread are configured such that rotation of the medicament delivery device relative to the needle assembly does not increase threaded engagement between the first thread and the second thread.

10. The needle assembly system according to claim 3, wherein the second thread and the third thread are configured to generate a tactile feedback that indicates that the needle assembly is mounted to the medicament delivery device.

11. The needle assembly system according to claim 3, wherein the depth of the third thread corresponds to a difference between a minor diameter and a major diameter of the third thread, and the depth of the first thread corresponds to a difference between a minor diameter and a major diameter of the first thread.

12. The needle assembly system according to claim 5, wherein the one or more ribs are configured to abut the second thread when the needle assembly is mounted on the medicament delivery device.

13. The needle assembly system according to claim 5, wherein the one or more ribs are configured to produce a biasing force between the needle assembly and the medicament delivery device as the needle assembly is mounted on the medicament delivery device.

14. The needle assembly system according to claim 1, wherein the first thread and the second thread are disengaged from each other when the needle assembly is mounted on the medicament delivery device.

15. The needle assembly system according to claim 1, wherein:
the needle assembly is configured to move proximally relative to the medicament delivery device when the first thread and the second thread are engaged and the needle assembly and the medicament delivery device are rotated relative to one another in a first direction about a longitudinal axis of the needle assembly, and
the needle assembly is configured to move distally relative to the medicament delivery device when the first thread and the second thread are engaged and the needle assembly and the medicament delivery device are rotated relative to one another in a second direction about the longitudinal axis of the needle assembly.

16. The needle assembly system according to claim 15, wherein the needle assembly is configured such that rotation of the needle assembly relative to the medicament delivery device in the first direction does not further tighten the needle assembly on the medicament delivery device when the needle assembly is mounted on the medicament delivery device.

17. The needle assembly system according to claim 1, wherein the distal portion of the medicament delivery device comprises the unthreaded region, and a distalmost thread of the medicament delivery device abuts a proximalmost thread of the needle assembly when the needle assembly is mounted on the medicament delivery device, the first thread comprising the distalmost thread, and the second thread comprising the proximalmost thread.

18. The needle assembly system according to claim 1, wherein the proximal portion comprises an unthreaded portion connected to the cover portion, the unthreaded portion extending from the cover portion to the first thread by at least the first distance.

19. A needle assembly comprising:
a needle;
a needle hub adapted to carry the needle, the needle hub comprising
   a proximal portion adapted to engage a distal portion of a medicament delivery device to mount the needle assembly on the medicament delivery device; and
   a cover portion adapted to abut a distal surface of the medicament delivery device,
wherein the proximal portion of the needle hub includes a second thread adapted to engage a first thread of the medicament delivery device,
wherein the second thread is offset from the cover portion by a first distance substantially equivalent to a second distance over which the first thread extends along the distal portion of the medicament delivery device such that the needle assembly is threadedly disengaged from the first thread of the medicament delivery device when the needle assembly is mounted on the medicament delivery device, and
wherein the second thread is configured to be positioned over (i) an unthreaded region of the medicament delivery device or (ii) a threaded region of the medicament delivery device having a third thread with a depth less than a depth of the first thread of the medicament delivery device, the second thread being configured such that rotation of the needle assembly relative to the medicament delivery device does not further tighten the needle assembly on the medicament delivery device when the needle assembly is mounted on the medicament delivery device.

20. The needle assembly of claim 19, wherein a distal end of the second thread is configured to be proximal to a proximal end of the first thread when the needle assembly is mounted on the medicament delivery device.

* * * * *